(12) United States Patent
Wahl et al.

(10) Patent No.: US 9,387,172 B2
(45) Date of Patent: Jul. 12, 2016

(54) SOLID DOSAGE FORM COMPRISING MICRONIZED CYTISINE AND ITS PRODUCTION METHOD

(71) Applicant: AFLOFARM FARMACJA POLSKA SPOLKA Z OGRANICZONA ODPOWIEDZIALNOSCIA, Pabianice (PL)

(72) Inventors: Hanna Wahl, Pabianice (PL); Marek Dabrowa, Lodz (PL); Piotr Kulazinski, Lodz (PL)

(73) Assignee: Aflofarm Farmacja Polska Sp. z o.o, Pabianice (PL)

( * ) Notice: Subject to any disclaimer, the term of this patent is extended or adjusted under 35 U.S.C. 154(b) by 0 days.

(21) Appl. No.: 14/443,584

(22) PCT Filed: Nov. 19, 2013

(86) PCT No.: PCT/IB2013/060230
§ 371 (c)(1),
(2) Date: May 18, 2015

(87) PCT Pub. No.: WO2014/076680
PCT Pub. Date: May 22, 2014

(65) Prior Publication Data
US 2015/0342884 A1      Dec. 3, 2015

(30) Foreign Application Priority Data

Nov. 19, 2012 (PL) ......................... 401676

(51) Int. Cl.
| | |
|---|---|
| *A61K 9/14* | (2006.01) |
| *A61K 9/48* | (2006.01) |
| *A61K 31/439* | (2006.01) |
| *A61K 31/435* | (2006.01) |

(52) U.S. Cl.
CPC .............. *A61K 9/146* (2013.01); *A61K 9/4825* (2013.01); *A61K 9/4866* (2013.01); *A61K 31/435* (2013.01); *A61K 31/439* (2013.01)

(58) Field of Classification Search
CPC ... A61K 9/146; A61K 9/4825; A61K 9/4866; A61K 31/435; A61K 31/439
See application file for complete search history.

(56) References Cited

U.S. PATENT DOCUMENTS

2006/0211649 A1      9/2006   Marchewitz

FOREIGN PATENT DOCUMENTS

| EP | 1 586 320 A1 | 10/2005 |
| EP | 2 233 134 A1 | 9/2010 |

OTHER PUBLICATIONS

International Search Report for PCT/IB2013/060230 dated Mar. 17, 2014.

*Primary Examiner* — Trevor Love
(74) *Attorney, Agent, or Firm* — Sughrue Mion, PLLC

(57) ABSTRACT

The subject of the present invention is solid dosage form containing cytisine and ancillary substances characterised in that it contains from 0.1% to 5% micronised cytisine, wherein all molecules have a diameter less than from 10 μπι, corn starch from 40% to 60%, preferably 99.9% particles sized from 5 μπι to 25 μπι, macrocrystalline cellulose in an amount from 40% to 60%, preferably the particle size is: 99% below 38 μπι, wherein the mass ratio of ancillary substances to the active ingredient is from 1:19 to 1:999 and is in the form of a hard capsule as well as a method of obtaining it.

12 Claims, No Drawings

SOLID DOSAGE FORM COMPRISING MICRONIZED CYTISINE AND ITS PRODUCTION METHOD

CROSS REFERENCE TO RELATED APPLICATIONS

This application is a National Stage of International Application No. PCT/IB2013/060230 filed Nov. 19, 2013, claiming priority based on Polish Patent Application No. PL401676 filed Nov. 19, 2012, the contents of all of which are incorporated herein by reference in their entirety.

The subject of the present invention is a solid dosage form containing micronised cytisine as well as a method of producing it. The present invention is useful in pharmacy as well as medicine.

There is a medicinal preparation to ease quitting smoking in the form of coated tablet with the trade name Tabex which contains 1.5 mg cytisine per tablet and ancillary substances: calcium bicarbonate, lactose, wheat starch, Avicel PH 101, powdered talcum, magnesium stearate and a coating. The tablet core composition does not ensure the stability of the coated tablet, nor does it give it sufficient mechanical resistance nor the necessary separation of the active ingredient. The resulting tablets have a low mechanical resistance and resistance to abrasion and to not fulfill the requirements set out in the European Pharamcopeia relating to the even dispersion and solubility of cytisine. Polish patent PL1586320 discloses a tablet containing cytisine, whose composition facilitates the homogenous dispersion of the active ingredient throughout the tablet, ensuring the high solubility of cytisine. In addition to cytisine, this product contains the following ancillary substances: lactose monohydrate, microcrystalline cellulose, talcum, magnesium stearate as well as an Opadry II coating, in the form of a tablet. Through the presence of lactose, the composition of the core prevents its use in patients with hereditary galactose intolerance, lactase insufficiency (Lapp-type) nor the poor galactose-lactose absorption syndrome, and may cause tablet instability due to the presence of a carboxyl group in the lactose molecule, which is not completely inert chemically and may lead to a Maillard reaction. This results in a brownish discoloration of the tablet. The method of producing the tablet also entails many complex physical processes/phenomena which may have a deleterious effect on the medicinal product. One of these phenomena is a high temperature during the tableting process which has a negative effect on cytisine stability during the process, which is evidenced by the initial results of contaminant content in the product encompassed by the above patent (PL1586320). Thus, there is still a need to obtain a pharmaceutical composition containing cytisine that eliminates the risk of the deleterious effects of the Maillard reaction, enclosed in a drug form that negates the negative effect of triturating forces on the tablet's mechanical stability, which additionally ensure a high degree of cytisine solubility as well as its stability and homogenous dispersion, which will be available to hereditary galactose intolerance. Unexpectedly, these problems have been solved by the present invention.

The first subject of the present invention is a solid dosage form containing cytisine and ancillary substances characterised in that it contains from 0.1% to 5% micronised cytisine, wherein all molecules have a diameter less than from 10 µm, corn starch from 40% to 60%, preferably 99.9% molecules sized from 5 µm to 25 µm, microcrystalline cellulose in an amount from 40% to 60%, preferably the molecular size is: 99% below 38 µm, wherein the mass ratio of ancillary to active substances is from 1:19 to 1:999 and is in the form of a hard capsule. Preferably, a solid dosage form according to the present invention contains coloidal silica in the amount of 0.4% as well as magnesium stearate and the capsule contains gelatine, titanium dioxide and indigotine.

The second subject of the present invention is a method of obtaining a hard capsule containing cytisine defined in the first subject of the present invention characterised in that it encompasses a) mixing micronised cytisine with a portion, preferably from 0.70% to 0.90%, of the microcrystalline cellulose necessary for the whole process, b) mixing the formed mixture from stage a) with a portion, preferably from 12% to 16% the remaining quantity of microcrystalline cellulose necessary for the whole process c) mixing the formed mixture from stage b) with the remaining quantity of microcrystalline cellulose necessary for the whole process as well as then the remaining ancillary substances to homogeneity d) encapsulation.

Equally preferably, a method according to the present invention is characterised in that in stage a) 0.79% are mixed and in stage b) 14.4% of the micronised microcrystalline cellulose.

The nature of the present invention is based on the formation of a homogenous mass of powdered substances (capsule mass), dosed into hard gelatine capsules containing a homogenously dispersed active ingredient, prepared without the use of increased moisture and temperature which ensures cytisine stability throughout the technological process. Additionally, the formulation without the use of lactose ensures therapeutic access to a broader group of recipients and decreases the risk of product discolouration due to the Maillard reaction. We produced a capsule mass according to the present invention dosed into hard gelatine capsules with the following content of the active ingredient (Table 1).

EXAMPLE NO. 1

A Method of Obtaining Capsules According to the Present Invention

A product being the subject of the present invention, whose preferable embodiment is shown in Table 1, was prepared according to the following production technology:

An appropriate mass of micronised cytisine was mixed with 0.79% the necessary amount of microcrystalline cellulose (of appropriate grain size), then added to a container which contained 14.4% of the necessary amount of microcrystalline cellulose of appropriate grain size, and the entirety was mixed.

The container was supplemented with the remaining amount of microcrystalline cellulose (of appropriate grain size) as well as a mixture of cytisine with microcrystalline cellulose, mixed and then added to corn starch (of appropriate grain size), colloidal silica and magnesium stearate. The container was placed on a mixing column and the contents were mixed. The capsule mass was dosed into hard gelatine capsules.

The requirements relating to ingredient dispersal were as follows:

cytisine: 100% below 10 µm, microcrystalline cellulose: 99% below 38 µm corn starch: 99.9% molecules in the range of 5 µm do 25 µm

TABLE 1

Composition of the subject product of the present invention:

| Item | Initial material | Quantity [mg] |
|---|---|---|
| 1. | Cytisine | 1.50 |
| 2. | Microcrystalline cellulose | 187.75 |
| 3. | Corn starch | 187.75 |
| 4. | Anhydrous coloidal silica | 1.50 |
| 5. | Magnesium stearate | 1.50 |

We obtained a homogenous capsule mass for dosing into hard gelatine capsules wherein the active ingredient contaminant content is below the level of detection due to the experimentally selected pharmaceutical composition, the appropriate dispersion of the composition components and the production technology used.

The selection of the appropriate composition in experimentally derived ratios and the use of the medicinal substance, microcrystalline cellulose and corn starch with an appropriate, experimentally derived grain size as well as the above described technology for forming the capsule mass enabled the hard capsule to attain a homogenous distribution of the active ingredient in the form of a drug, with out the use of production stages connected with increased temperature and moisture.

Additionally, the use of corn starch, microcrystalline cellulose as well as colloidal silica ensures protection of the active ingredient against the deleterious effects of the external environment during the technological process (Example No. 2) and the formulation not makings use of lactose increases the applicability of the preparation and prevents discolouration via the Maillard reaction.

Acceptance criteria of the present invention were: a low level (below the detection threshold) of active ingredient contaminants of the final drug form at the end of the technological process (experimental description illustrated in Example No. 3), homogeneity of the active ingredient dispersion in the capsule mass (experimental description given in Example No. 4.) as well as a high solubility of cytisine from the complete drug form (bioavailability)of cytisine (experimental description given in Example No. 5.)

EXAMPLE NO. 2

Cytisine stability depending on the ancillary substances used during stability stress testing.

The disclosed composition of the present invention ensures the best active ingredient stability during stress testing. We determined acceptance criteria: lowest degree of active ingredient contamination during the storage of the active ingredient under stress conditions: temp. 60° C. and time—two weeks.

We prepared mixtures of substances of the following compositions:

2a: composition according to the composition of the present invention (Example No. 1)

2b: analogous composition to 2a except that instead of corn starch we used potato starch 2c: analogous composition to 2a except that instead of corn starch we used potato starch, and the microcrystalline cellulose was replaced with lactose monohydrate;

2d: analogous composition to 2a except that instead of microcrystalline cellulose we used lactose monohydrate.

2e: analogous composition to 2a except that instead of corn starch we used lactose monohydrate, and the mass ratio of lactose to microcrystalline cellulose was 1:2 (analogously as in Example 1 of patent PL1586320).

Unexpectedly it turned out that there are significant differences in the contaminant levels of the active ingredient at the end of the test, these results are shown in Table 2a.

TABLE 2a

Contaminant content of the active ingredient at the end of the stability stress test.

| | | Contaminant content (percent) in relation to cytisine | |
|---|---|---|---|
| Item | Sample | Each | Summary |
| 1. | 2a | 0.16 | 0.16 |
| 2. | 2b | 0.18 | 0.50 |
| 3. | 2c | 0.21 | 0.33 |
| 4. | 2d | 0.16 | 0.27 |
| 5. | 2e | 0.14 | 0.35 |

The best protection for the active ingredient during the stress test (lowest contaminant growth) is afforded by the composition being the subject of the present invention (Table 1; sample 1a). Unexpectedly it turned out that in addition to the lowest summary contaminant level in comparison to the other combinations, only in this case we observed the presence of a single contaminant.

EXAMPLE NO. 3

Cytisine Stability Throughout the Technological Process

The disclosed technical process ensures the lowest (below the detection threshold) contaminant level of the active ingredient in the complete drug.

We established an acceptance criterion: contaminant level below the limit of detection (LOD)

The capsule mass (composition according to Table 1, Example No. 1) was prepared using two alternative methods; the first (P3a) encompassed granulation and drying at 50° C. The second method of preparing the capsule mass (P3b) described in the nature of this patent did not require the use of solvents, nor of high temperatures.

We obtained the following results of active ingredient contaminant levels Table 3a.

TABLE 3a

Contaminant content of the active ingredient in the complete drug form during the experimental procedures

| | | Result | |
|---|---|---|---|
| Item | Sample | N-formyl-cytisine (percent in relation to cytisine) | Summary contaminants (percent) in relation to cytisine |
| 1. | P3a | 0.29 | 0.36 |
| 2. | P3b | LOD* | LOD* |

*below the detection limit

The use of the capsule mass preparation technology described in the nature of the present invention significantly affects the decrease of active ingredient contamination in comparison to wet granulation.

EXAMPLE NO. 4

Homogeneity of cytisine dispersion in the capsule mass.

The disclosed composition and technological process facilitate the production of a capsule mass homogenous in terms of active ingredient content, dosed into gelatine capsules via a hard capsule at a level below 3%

This part of the present invention entailed a need to perform the following experiments:

4a) Determination of the amount as well as size of the grains of the active ingredient.

The capsule mass (composition according to Table 1, Example No. 1) was prepared using two alternative active ingredient grain sizes as well as different amounts of cytisine. Sample P4a1 was prepared using an active ingredient grain size of 100%<80 mesch (180 μm), whereas sample P4a2 was prepared using micronised active ingredient (100% particles below 10 μm); according to the present invention. Sample P4a3 was prepared according to the composition and technology described in Table 1, Example No. 1 with the exception that the amount of active ingredient was 0.38 mg/380 mg and analogously in sample P4a4 except that the amount of active ingredient was 19 mg/380 mg of capsule mass; the remaining substances as well as the method of preparing were according to the present invention. The content of the active ingredient in samples of capsule mass collected from different parts of the mixer (three samples each from three levels of the capsule mass, three weigh-offs of 380 mg were prepared from each sample) is illustrated in Table 4a1.

TABLE 4a1

Cytisine content in samples collected after mixing the capsule mass.

| Item | P4a1 | P4a2 | P4a3 | P4a4 |
|---|---|---|---|---|
| 1. | 1.47 | 1.54 | 1.53 | 1.49 |
| 2. | 1.50 | 1.48 | 1.52 | 1.46 |
| 3. | 1.37 | 1.52 | 1.47 | 1.48 |
| 4. | 1.38 | 1.50 | 1.43 | 1.51 |
| 5. | 1.39 | 1.57 | 1.52 | 1.49 |
| 6. | 1.50 | 1.46 | 1.57 | 1.45 |
| 7. | 1.54 | 1.53 | 1.52 | 1.53 |
| 8. | 1.57 | 1.51 | 1.50 | 1.48 |
| 9. | 1.52 | 1.46 | 1.44 | 1.48 |
| 10. | 1.44 | 1.56 | 1.47 | 1.45 |
| 11. | 1.37 | 1.51 | 1.56 | 1.43 |
| 12. | 1.47 | 1.50 | 1.51 | 1.52 |
| 13. | 1.52 | 1.47 | 1.49 | 1.50 |
| 14. | 1.32 | 1.52 | 1.53 | 1.51 |
| 15. | 1.42 | 1.47 | 1.46 | 1.48 |
| 16. | 1.49 | 1.55 | 1.57 | 1.53 |
| 17. | 1.45 | 1.52 | 1.47 | 1.52 |
| 18. | 1.51 | 1.48 | 1.57 | 1.45 |
| 19. | 1.46 | 1.49 | 1.47 | 1.46 |
| 20. | 1.44 | 1.54 | 1.53 | 1.48 |
| 21. | 1.49 | 1.56 | 1.57 | 1.49 |
| 22. | 1.45 | 1.46 | 1.48 | 1.52 |
| 23. | 1.55 | 1.48 | 1.46 | 1.49 |
| 24. | 1.45 | 1.52 | 1.49 | 1.46 |
| 25. | 1.47 | 1.51 | 1.53 | 1.50 |
| 26. | 1.44 | 1.46 | 1.54 | 1.45 |
| 27. | 1.55 | 1.53 | 1.42 | 1.40 |
| $X^1$ | 1.46407 | 1.50741 | 1.50444 | 1.48185 |
| $S^2$ | 0.06185 | 0.03369 | 0.04449 | 0.03187 |
| $RSD^3$ | 4.22432 | 2.23527 | 2.95733 | 2.15066 |

$X^1$—average
$S^2$—standard deviation
$RSD^3$—relative standard deviation

The sample prepared using micronised cytisine is characterised by a high homogeneity of the active ingredient therein, in contrast to the sample prepared using standard-sized cytisine grains.

4b) Determination of the appropriate ancillary substance proportions

The determined composition facilitates the appropriate proportions of ancillary substances as well as their sufficient dispersal in the case of ancillary substances present in largest quantities.

During the experiment we tested formulations of capsule masses containing different proportions and grain sizes of microcrystalline cellulose as well as corn starch:

4b1: composition according to the composition of the present invention (Example No. 1) except that we used microcrystalline cellulose of standard grain size (average grains of 100 μm), 4b2: composition according to the composition of the present invention (Example No. 1) except that we used corn starch with a standard (from 25 μm to 32 μm) grain size 4b3 composition according to the composition of the present invention (Example No. 1) except that we used the following amount of microcrystalline cellulose—152 mg/380 mg and corn starch 228 mg/380 mg 4b4 composition according to the composition of the present invention (Example No. 1) except that we used the following amount of microcrystalline cellulose—228 mg/380 mg and corn starch 152 mg/380 mg.

It turned out that the samples (4b1 and 4b2) prepared using grains sizes different from those according to the present invention did not yield satisfactory results, whereas the remaining sample results as in the present invention (4b3 and 4b4) gave results within approved acceptance criteria. This is shown by the results shown in Table 4b:

TABLE 4b

Cytisine content in the final drug form.

| Item | P4b1 | P4b2 | P4b3 | P4b4 |
|---|---|---|---|---|
| 1. | 1.44 | 1.47 | 1.49 | 1.48 |
| 2. | 1.49 | 1.49 | 1.44 | 1.59 |
| 3. | 1.37 | 1.38 | 1.50 | 1.52 |
| 4. | 1.39 | 1.54 | 1.51 | 1.44 |
| 5. | 1.39 | 1.42 | 1.41 | 1.54 |
| 6. | 1.50 | 1.48 | 1.44 | 1.46 |
| 7. | 1.54 | 1.51 | 1.46 | 1.54 |
| 8. | 1.57 | 1.50 | 1.44 | 1.53 |
| 9. | 1.52 | 1.52 | 1.44 | 1.47 |
| 10. | 1.44 | 1.49 | 1.45 | 1.46 |
| 11. | 1.58 | 1.58 | 1.42 | 1.43 |
| 12. | 1.47 | 1.46 | 1.44 | 1.51 |
| 13. | 1.52 | 1.38 | 1.43 | 1.52 |
| 14. | 1.38 | 1.58 | 1.44 | 1.48 |
| 15. | 1.46 | 1.48 | 1.42 | 1.48 |
| 16. | 1.48 | 1.47 | 1.52 | 1.52 |
| 17. | 1.51 | 1.52 | 1.52 | 1.52 |
| 18. | 1.51 | 1.58 | 1.50 | 1.46 |
| 19. | 1.46 | 1.56 | 1.50 | 1.44 |
| 20. | 1.47 | 1.46 | 1.52 | 1.49 |
| 21. | 1.49 | 1.48 | 1.48 | 1.48 |
| 22. | 1.48 | 1.52 | 1.49 | 1.53 |
| 23. | 1.51 | 1.52 | 1.55 | 1.48 |
| 24. | 1.45 | 1.45 | 1.54 | 1.43 |
| 25. | 1.47 | 1.49 | 1.55 | 1.51 |
| 26. | 1.37 | 1.43 | 1.41 | 1.47 |
| 27. | 1.54 | 1.39 | 1.49 | 1.53 |
| $X^1$ | 1.47407 | 1.48704 | 1.47407 | 1.49296 |
| $S^2$ | 0.05766 | 0.05642 | 0.04388 | 0.03930 |
| $RSD^3$ | 3.91184 | 3.79411 | 2.97649 | 2.63255 | where:
$X^1$—average
$S^2$—standard deviation
$RSD^3$—relative standard deviation

EXAMPLE NO. 5

Cytisine solubility from the final drug form.

The disclosed composition the present invention as well as the technological process ensure the rapid dissolution rate of cytisine from the final drug form. The comparison product used was Tabex s: 4041011.

The designated acceptance criterion was the active ingredient dissolution time from the final drug form in an acceptor fluid, which was 0.1 mol/l hydrochloric acid imitating the conditions found in the human stomach.

We loaded the bottom of a beaker containing 0.1 mol/l hydrochloric acid with a single tablet of Tabex, and in another a single gelatine capsule prepared according to the composition and technology described in Example No. 1 (P5). During mixing, we collected samples of the acceptor solution at the following time points: after 5 min., 7.5 min, 10.0 min as well as 12.5 min. The cytisine content in the acquired samples is illustrated in Table 5a.

TABLE 5a

Cytisine content in the acceptor solution depending on time.

| Experimental time | Solubility in % w 0.1 mol/l HCl | |
| --- | --- | --- |
| | Tabex | P5 |
| 5 min. | 23.8 | 39.4 |
| 7.5 min. | 46.0 | 62.5 |
| 10.0 min. | 62.9 | 74.4 |
| 15.0 min | 74.7 | 81.1 |

Unexpectedly it turned out that cytisine from the final drug form described in the present invention dissolves faster than from a tablet defined in PL1586320 and present on the market.

The invention claimed is:

1. A solid dosage form containing cytisine and ancillary substances, wherein the solid dosage form contains:
   from 0.1% to 5% micronised cytisine, wherein all molecules have a diameter less than 10 μm,
   corn starch from 40% to 60%, and
   microcrystalline cellulose in an amount from 40% to 60%, and
   wherein the mass ratio of the active ingredient to ancillary substances is from 1:19 to 1:999 and is in the form of a hard capsule.

2. The solid dosage form according to claim 1 characterised in that it contains colloidal silica in the amount of 0.4% as well as magnesium stearate and the capsule contains gelatine, titanium dioxide and indigotine.

3. A method of obtaining a hard capsule containing cytisine, defined in claim 1 comprising:
   a) mixing micronised cytisine with a portion of the microcrystalline cellulose necessary for the whole process,
   b) mixing the formed mixture from step a) with a portion of the remaining quantity of microcrystalline cellulose necessary for the whole process,
   c) mixing the mixture from step b) with the remaining quantity microcrystalline cellulose necessary for the whole process as well as the remaining ancillary substances to homogeneity; and
   d) encapsulation.

4. The method according to claim 3 characterised in that in stage a) 0.79% and in stage b) 14.4% of the micronised microcrystalline cellulose is mixed.

5. A method of obtaining a hard capsule containing cytisine, defined in claim 2 comprising:
   a) mixing micronised cytisine with a portion of the microcrystalline cellulose necessary for the whole process,
   b) mixing the formed mixture from step a) with a portion of the remaining quantity of microcrystalline cellulose necessary for the whole process,
   c) mixing the mixture from step b) with the remaining quantity microcrystalline cellulose necessary for the whole process as well as the remaining ancillary substances to homogeneity; and
   d) encapsulation.

6. The method according to claim 5 characterised in that in stage a) 0.79% and in stage b) 14.4% of the micronised microcrystalline cellulose is mixed.

7. The solid dosage form according to claim 1 wherein 99.9% of the corn starch particles are sized particles sized from 5 μm to 25 μm.

8. The solid dosage form according to claim 1 99% of the microcrystalline cellulose particles are sized below 38 μm.

9. The method of obtaining a hard capsule containing cytisine according to claim 3 wherein the portion of the microcrystalline cellulose necessary for the whole process in step b) is from 0.70% to 0.90%.

10. The method of obtaining a hard capsule containing cytisine according to claim 3 wherein the portion of the remaining quantity of microcrystalline cellulose necessary for the whole process is 12% to 16%.

11. The method of obtaining a hard capsule containing cytisine according to claim 5 wherein the portion of the microcrystalline cellulose necessary for the whole process in step b) is from 0.70% to 0.90%.

12. The method of obtaining a hard capsule containing cytisine according to claim 5 wherein the portion of the remaining quantity of microcrystalline cellulose necessary for the whole process is from 12% to 16%.

\* \* \* \* \*